United States Patent [19]
Lyon et al.

[11] Patent Number: 5,514,671
[45] Date of Patent: May 7, 1996

[54] ALTERNATIVE ENZYME SUBSTRATES AS DEODORANTS

[75] Inventors: Sue B. Lyon, Bethesda; Clifford O'Neal, Gaithersburg; Hermes van der Lee, Olney, all of Md.

[73] Assignee: The Gillette Company

[21] Appl. No.: 89,599

[22] Filed: Jul. 12, 1993

Related U.S. Application Data

[63] Continuation of Ser. No. 824,884, Jan. 22, 1992, abandoned, which is a continuation of Ser. No. 685,161, Apr. 12, 1991, abandoned, which is a continuation of Ser. No. 478,363, Feb. 12, 1990, abandoned.

[51] Int. Cl.$^6$ .................................................. A61K 7/32
[52] U.S. Cl. ............................................ 514/104; 424/65
[58] Field of Search ................................ 514/104; 424/65

[56] References Cited

U.S. PATENT DOCUMENTS 5,213,791  5/1993  Lyon et al. ............................ 424/65

OTHER PUBLICATIONS

Chem. Abs., Apr. 1973, vol. 78 pp. 84815r, Klosa.
Chem. Abs. Jul. 1975, vol. 83(4), pp. 32923H, Mitomo.
Chem. Abs., Oct. 1977, vol. 87(16), pp. 122645f, Bore.
Chem. Abs., Dec. 1985, vol. 103(24), pp. 200711g, Takasago.
Chem. Abs., Dec. 1987, vol. 108(22) pp. 188398m, Ono.
Chem. Abs., Apr. 1989, vol. 110 (16), pp. 1412241c, Sato.
Chem. Abs., 1988, vol. 111(16), pp. 140549r, Inoue.
Chem. Abs., 1989, vol. 113(8) pp. 64563V, Hirata et al.

*Primary Examiner*—Shelley A. Dodson
*Assistant Examiner*—Michael A. Williamson
*Attorney, Agent, or Firm*—Burns, Doane, Swecker & Mathis

[57] ABSTRACT

The invention relates to a method of suppressing human body malodor by utilizing a deodorant composition containing a competitive substrate for the enzymatic creation of axillary body malodor.

10 Claims, No Drawings

ALTERNATIVE ENZYME SUBSTRATES AS DEODORANTS

This application is a continuation, of application Ser. No. 07/824,884, filed Jan. 22, 1992 now abandoned, which is a continuation, of application Ser. No. 07/685,161, filed Apr. 12, 1991 now abandoned, which is a continuation, of application Ser. No. 07/478,363, filed Feb. 12, 1990 now abandoned.

BACKGROUND OF THE INVENTION

The present invention relates to deodorants, and a method of suppressing human body odor.

The eccrine and apocrine sweat glands are the structures of the human body responsible for sweat. The apocrine glands become active at puberty and produce an odorless proteinaceous secretion. Axillary bacteria act on the apocrine secretions to produce the pungent odor known as axillary malodor.

Current deodorants are generally of three types: odor maskers, antiperspirants, and germicides. Despite the many disclosures in the art pertaining to deodorant compositions, current products are not sufficient to suppress odor in a significant proportion of the population, particularly during periods of "stress." There remains a need for new deodorant compositions and methods which are effective, safe and economical.

SUMMARY OF THE INVENTION

The current invention is a deodorant composition comprising a compound which is capable of serving as an alternative substrate to the naturally occurring malodor producing precursor. The compound is present in a dermatologically acceptable vehicle, and in an amount effective to reduce the conversion of malodor producing precursor.

DETAILED DESCRIPTION OF THE INVENTION

The current invention is a novel method of suppressing body odor by the topical application of compounds which compete with the naturally occurring malodor producing precursor. Preferred compounds are amino acids and amino acid analogues. Deodorant compositions containing at least one compound from the specified groups of amino acids or amino acid analogues in an effective concentration will serve to suppress axillary malodor when applied to the underarm. Tests indicate that these compositions significantly attenuate the body odors formed in the axilla. In a preferred embodiment, the amino acids or amino acid analogues generate pleasant odors in the axilla concomitant with suppressing the malodor.

Axillary malodor is generated by certain skin bacteria in the presence of apocrine secretion. Two strains of bacteria which produce axillary malodor when incubated with human apocrine secretions are Staphylococcus and several Coryneform isolates. Production of human axillary malodor can be assayed from these strains of bacteria by incubating cells with apocrine secretions collected from human axilla that has been sterilized in a phosphate buffer at pH 6.8. The volatile malodor compound is extracted into chloroform and smelled after spotting on filter paper.

The conversion of apocrine precursor to axillary malodor occurs within the bacterial cells. Extracts of bacteria are capable of converting the precursor to the malodor compound in an enzymatic process. The enzyme which is designated as the malodor-forming enzyme has been found to be a pyridoxal phosphate dependent amino acid lyase. The enzyme acts to cleave amino acids with the general structure $HOOC—CH(NH_2)—CH_2—X$ where X is $—S—R$ or $O—R$. The products of the reaction are pyruvate, ammonia, and XH.

The apocrine precursor to axillary malodor is a sulfur containing amino acid. It has now been found that the production of axillary malodor is blocked if an alternative substrate for the malodor-forming enzyme is provided, so that the alternative substrate is cleaved instead of the apocrine precursor. The alternative substrates produce either a neutral odor or a pleasant odor upon cleavage.

Certain amino acids and amino acid analogues can serve as deodorants in this fashion, i.e., these amino acids and amino acid analogues serve as alternative substrates for malodor-forming enzyme and produce a neutral or pleasant odor. As stated above, the malodor-forming enzyme cleaves amino acids and amino acid analogues having the general structure, $HOOC—CH(NH_2)—CH_2—X$ where X is $S—R$ or $O—R$. In the present invention, amino acids or amino acid analogues are employed with an R group which results in the production of neutral or pleasant odors. The R group may be a) a branched or straight alkyl chain of one to about ten carbon atoms that may be substituted with one or more hydroxyl, amino, carboxyl, or phenyl groups; or b) an aromatic ring that is unsubstituted or substituted with one or more hydroxyl, amino, or carboxyl groups, or an aliphatic carbon chain of one to about eight carbon atoms. For example, the enzyme cleaves O-benzylserine (i.e., where X is O-benzyl) to produce non-odorous benzyl alcohol. The compounds ethyl serine, butyl serine, and S-O-nitrophenyl cysteine are other examples of such substrates.

The presence of the alternative substrates in adequate quantities will compete with the natural precursor and at least reduce, if not almost entirely prevent its conversion.

In addition, when certain of these alternative substrates are cleaved, pleasant odors are produced. These amino acids and amino acid analogues are generally those in which R is an aromatic or branched chain aliphatic group. The alcohol that results from cleavage is pleasant smelling. The compound O-phenethylserine which is converted to phenethyl alcohol, a compound that smells of rose, and the compound O-menthylserine which converts to menthol, are two examples of such cleavage products. Other such compounds are O-3-phenylpropylserine and O-1-octenyl-3-serine.

The presence of an alternative substrate such as the above in large quantities competes with the natural precursor which is present in low quantities, typically about one nanomole/axilla. Such competition almost completely prevents the malodor precursor from being converted. These compounds therefore serve as deodorants.

Although deodorancy is the most important concern for the consumer of underarm products, many also choose a product with antiperspirant activity. Current antiperspirants, which are aluminum salts, also function as deodorants by virtue of their germicidal properties. Thus, if desired, the deodorants of the present invention can be employed with the antiperspirant compounds well known in the art. In such formulations, the alternative substrates, such as the specified amino acids and amino acid analogues of the present invention can be incorporated into an antiperspirant formulation with the antiperspirant being employed in a perspiration reducing effective concentration.

The antiperspirant component used in the present invention may be any of those which contain aluminum, either alone or in combination with other materials such as zirconium. Typical aluminum salts, although not all-inclusive, include:

Aluminum chlorohydrate;
Aluminum sesquichlorohydrate;
Aluminum dichlorohydrate;
Aluminum chlorohydrex PG or PEG;
Aluminum sesquichlorohydrex PG or PEG;
Aluminum dichlorohydrex PG or PEG;
Aluminum zirconium trichlorohydrate;
Aluminum zirconium tetrachlorohydrate;
Aluminum zirconium tetrachlorohydrex PG or PEG;
Aluminum zirconium pentachlorohydrate;
Aluminum zirconium octachlorohydrate;
Aluminum zirconium trichlorohydrex-gly;
Aluminum zirconium tetrachlorohydrex-gly;
Aluminum zirconium pentachlorohydrex-gly;
Aluminum zirconium octachlorohydrex-gly;
Aluminum zirconium chloride;
Aluminum zirconium sulfate;
Potassium aluminum sulfate;
Sodium aluminum chlorohydroxylacetate;
Aluminum bromohydrate.

In general the active antiperspirant component should be present in the same amounts at which such materials are employed in prior art compositions. As a general rule, the antiperspirant composition should contain from about 5% to about 30%, preferably from about 10 to 25% of the active antiperspirant salt component.

In order to further illustrate the present invention and the advantages thereof, the following specific examples are given. It is understood that these examples are intended only to be illustrative without serving to limit the scope of the present invention.

Example I

Evaluation of cysteine analogues and serine analogues that produce odorless products.

As a representative of cysteine analogues, S-O-nitrophenyl cysteine was evaluated. S-O-nitrophenyl cysteine inhibited the formation of malodor in the assay described above at concentrations of 0.1 to 10 mM by serving as an alternative substrate. Inhibition was complete at concentrations over 3 mM. When tested for the ability to block malodor formation when whole bacterial cells were used in the malodor assay, the minimal concentration needed for complete inhibition was 100 µm.

As a representative of serine analogues, O-benzyl serine was found to be effective as a substrate of the malodor enzyme at concentrations of 0.1 to 1 mM.

Example II

Evaluation of serine analogues that concomitantly produce a pleasant odor.

Among serine analogues, O-phenethyl serine was tested for the ability to inhibit malodor in vitro by serving as an alternative substrate. O-Phenethylserine inhibited malodor production completely at concentrations over 50 µM. The compound was effective in the inhibition of malodor in the presence of whole bacterial cells at concentrations greater than 5 mM. O-Phenethylserine was tested in the axilla of humans in a deodorancy clinical trial and found to be efficacious in producing a pleasant odor at 1.4% in 50% propylene glycol/water. Phenethyl alcohol was produced at detectable levels.

Formulations for Deodorant Use

The concentration of amino acid or amino acid analogue employed in topical applications should be consistent with efficacy, economy and safety. The amino acids and amino acid analogues of the present invention are employed in a malodor precursor competing amount, and are efficacious at concentrations between about 5 micromolar and 500 millimolar, i.e., about 0.01% to about 10% by weight. The preferred range is from about 0.01–200 millimolar. The most preferred range is from about 0.05–50 millimolar. This constitutes a weight percent of about 0.1% to 1% by weight as the most preferred range of active ingredient.

If desired, the amino acid or amino acid analogue of the present invention can also be employed in combination with an antiperspirant. In such case, the amino acid or amino acid analogue is merely added to the standard formulation for the antiperspirant composition in the same concentrations as set forth above.

Examples of formulations are given below:

| 1. Deodorant Stick | % by weight |
|---|---|
| propylene glycol | 78 |
| sodium stearate C-1 | 7.9 |
| fragrance | 0.1 |
| water | 13 |
| phenethylserine | 1 |

Procedure: Mix propylene glycol and sodium stearate C-1 at room temperature and stir. Increase the temperature to about 70° C. and continue agitation to obtain a clear and uniform solution. Add the water followed by the phenethylserine. Lower the temperature to 55° C. and add the fragrance. Pour into molds and cool to room temperature.

| 2. Deodorant Roll-on Emulsion | % by weight |
|---|---|
| hydrogenated palm oil glycerides and sodium cetyl sulfate | 3.0 |
| steareth-7 | 1.0 |
| octyldodecanol | 4.0 |
| glyceryl laurate | 2.0 |
| octyl palmitate | 4.0 |
| dimethicone | 1.0 |
| propylparaben | 0.1 |
| methylparaben | 0.2 |
| imidazolidinyl urea | 0.3 |
| glycerin | 5.0 |
| allantoin | 0.5 |
| PEG-35 lanolin | 0.5 |
| fragrance | 0.3 |
| 2 wt. % phenethylserine acid in 80% propylene glycol/20% water at neutral pH | 78.1 |

Procedure: Mix and stir the ingredients except the fragrance at 80° C. Decrease the temperature to 40° C. and add the fragrance. Decrease the temperature to room temperature.

| 3. Aerosol Deodorant | % by weight |
|---|---|
| zinc phenolsulfonate | 1.7 |
| quaternium 18 hectorite | 1.0 |
| dioctyl succinate | 10.0 |
| SDA 40 ethanol, anhydrous | 20.0 |
| fragrance | 0.1 |
| 1 wt. % phenethylserine in 50% ethanol/water at neutral pH | 10.0 |
| propellant | 57.2 |

Procedure: Dissolve all ingredients in the alcohol, add the propellant, and cold or pressure fill.

| 4. Roll-On Antiperspirant and Deodorant | % by weight |
|---|---|
| PPG-15 stearyl ether | 4.0 |
| steareth-21 | 0.6 |
| steareth-2 | 2.6 |
| aluminum zirconium pentachlorohydrate, 10:1 (a 25% solution) | 32.0 |
| fragrance | 0.1 |
| 1.8 wt % phenethylserine in 80% propylene glycol/water at neutral pH | 60.7 |

Procedure: Mix all the ingredients except the fragrance at 70° C. with agitation. Add the fragrance at 45° C. Stir and cool to room temperature.

| 5. Aerosol Antiperspirant and Deodorant | % by weight |
|---|---|
| phenethylserine | 1.0 |
| isopropyl myristate | 13.4 |
| aluminum chlorohydrate | 10.0 |
| quaternium-18 hectorite | 0.8 |
| SDA 40 ethanol, anhydrous | 0.8 |
| fragrance | 0.1 |
| propellant | 73.9 |

Procedure: Mix the isopropyl myristate and quaternium-18 hectorite together for 30 minutes with an Eppenbach Homomixer. Add aluminum chlorohydrate and mix 15 minutes. Add the phenethylserine and SDA 40 and mix 10 minutes. Homogenize the suspension using a Manton-Gaulin homogenizer set at 6000 psi. Add fragrance and mix on a Hobart Mixer set at moderate speed. Mix 10 minutes. Charge with propellant.

| 6. Stick Antiperspirant and Deodorant | % by weight |
|---|---|
| aluminum chlorohydrate | 16.0 |
| SDA 40 ethanol, anhydrous | 30.0 |
| sorbitol, 70% | 3.0 |
| sodium stearate C-1 | 5.0 |
| sodium ceteth-13 carboxylate | 3.0 |
| stearyl alcohol | 1.0 |
| cyclomethicone | 15.0 |
| fragrance | 0.1 |
| 2 wt. % phenethylserine in 80% propylene glycol/water at neutral pH | 26.9 |

Procedure: Mix the aluminum chlorohydrate, SDA 40 ethanol and the phenethylserine and heat to 65° C. Add sorbitol and then sodium stearate C-1 and sodium ceteth-13 carboxylate, and mix until a complete solution is obtained. Add the remaining ingredients and mix for 5 min. Cool to 50° C. and add to containers.

While the invention has been described in terms of various embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A deodorant composition comprising an axillary malodor-suppressing effective amount of a compound of the structure

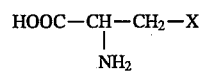

where X is O—R, and R is a) a branched or straight alkyl chain of one to about ten carbon atoms that may be substituted with one or more hydroxyl, amino, carboxyl, or phenyl groups; or b) an aromatic ring that is unsubstituted or substituted with one or more hydroxyl, amino, or carboxyl groups, or an aliphatic carbon chain of one to about eight carbon atoms, in a dermatologically acceptable vehicle.

2. The deodorant composition of claim 1 wherein the compound is O-benzylserine, ethyl serine, butyl serine.

3. The deodorant composition of claim 1 wherein the analogue is O-phenethylserine, O-menthylserine, O-3-phenylpropylserine, or O-1-octenyl-3-serine.

4. The deodorant composition of claim 1 wherein the compound is present at a concentration of at least about 0.01% by weight.

5. The deodorant composition of claim 1 wherein the compound is present at a concentration of between about 5 micromolar and about 500 millimolar.

6. The deodorant composition of claim 1 wherein the concentration of the compound is about 0.01–200 millimolar.

7. The deodorant composition of claim 1 wherein the concentration of the compound is about 0.05–50 millimolar.

8. The deodorant composition of claim 1, further comprising an antiperspirant salt.

9. A method of suppressing body malodor comprising the application to skin of the composition of claim 4, 5 or 1.

10. The deodorant composition of claim 1 wherein the compound is present at a concentration of about 0.01% to about 10% by weight.

* * * * *

UNITED STATES PATENT AND TRADEMARK OFFICE
CERTIFICATE OF CORRECTION

PATENT NO.  : 5,514,671
DATED       : May 7, 1996
INVENTOR(S) : Sue B. Lyon, et al It is certified that error appears in the above-indentified patent and that said Letters Patent is hereby corrected as shown below:

Col. 6, line 33, insert -- or -- before "butyl";
line 35, delete "analogue" and insert -- compound -- therefor.

Signed and Sealed this

Sixth Day of August, 1996

Attest:

BRUCE LEHMAN

Attesting Officer

Commissioner of Patents and Trademarks